US008591945B2

(12) United States Patent
Vandecruys et al.

(10) Patent No.: US 8,591,945 B2
(45) Date of Patent: Nov. 26, 2013

(54) PREGELATINIZED STARCH IN A CONTROLLED RELEASE FORMULATION

(75) Inventors: Roger Petrus Gerebern Vandecruys, Beerse (BE); Eugene Marie Jozef Jans, Beerse (BE)

(73) Assignee: Janssen Pharmaceutica, N.V., Beerse (BE)

( * ) Notice: Subject to any disclaimer, the term of this patent is extended or adjusted under 35 U.S.C. 154(b) by 745 days.

(21) Appl. No.: 12/416,219

(22) Filed: Apr. 1, 2009

(65) Prior Publication Data

US 2009/0191266 A1 Jul. 30, 2009

Related U.S. Application Data

(63) Continuation of application No. 10/674,701, filed on Sep. 30, 2003, now abandoned, which is a continuation of application No. 09/937,860, filed on Sep. 28, 2001, now Pat. No. 6,667,060.

(30) Foreign Application Priority Data

Mar. 31, 1999 (EP) .................................. 992010181

(51) Int. Cl.
*A61K 9/52* (2006.01)
(52) U.S. Cl.
USPC .......................................... 424/468; 424/464
(58) Field of Classification Search
USPC .................................................. 424/465–501
See application file for complete search history.

(56) References Cited

U.S. PATENT DOCUMENTS

| 3,459,731 | A |   | 8/1969  | Gramera et al.   |         |
|-----------|---|---|---------|------------------|---------|
| 4,806,359 | A |   | 2/1989  | Radebaugh et al. |         |
| 5,132,116 | A |   | 7/1992  | Sournac et al.   |         |
| 5,200,193 | A |   | 4/1993  | Radebaugh et al. |         |
| 5,334,393 | A |   | 8/1994  | Bougaret et al.  |         |
| 5,462,747 | A |   | 10/1995 | Radebaugh et al. |         |
| 5,534,496 | A |   | 7/1996  | Lee et al.       |         |
| 5,605,889 | A | * | 2/1997  | Curatolo et al.  | 514/29  |
| 5,635,208 | A |   | 6/1997  | Parekh et al.    |         |
| 5,670,158 | A |   | 9/1997  | Davis et al.     |         |
| 5,698,226 | A |   | 12/1997 | Fielden          |         |
| 5,792,477 | A | * | 8/1998  | Rickey et al.    | 424/501 |
| 5,824,339 | A | * | 10/1998 | Shimizu et al.   | 424/466 |
| 5,972,373 | A |   | 10/1999 | Yajima et al.    |         |
| 6,667,060 | B1|   | 12/2003 | Vandecruys et al.|         |

FOREIGN PATENT DOCUMENTS

| EP | 0280613    | B1 | 8/1988  |
|----|------------|----|---------|
| EP | 0299877    | B1 | 1/1989  |
| EP | 0477061    | B1 | 5/1995  |
| GB | 2195893    | A  | 4/1988  |
| WO | WO 95/08993| A1 | 4/1995  |
| WO | WO 96/14070| A1 | 5/1996  |
| WO | WO 97/04752| A1 | 2/1997  |
| WO | WO 97/04753|    | 2/1997  |
| WO | WO 97/24109| A1 | 7/1997  |
| WO | WO 97/44039| A1 | 11/1997 |
| WO | WO 99/16442|    | 4/1999  |

OTHER PUBLICATIONS

Abstract, JP 09052832A, Feb. 25, 1997, Takeda Chem Ind Ltd. "Vitamin compsn. which reduces sulphurous bad breath—contains vitamin B1 disulphide deriv., vitamin-B2 deriv. and hydroxypropyl-cellulose with low degree of substitution", Database WPI, Section Ch, Week 9718, Derwent Publications Ltd., London, GB.
"Formulating for controlled release with Methocel Premium cellulise ethers," published by the Dow Chemical Company in 1995, Form No. 198-1029-1295.
Visavarungroj, N. et al., "Crosslinked starch as sustained release agent," Drug Development and Industrial Pharmacy, 1990, 16(7), 1091-1108.
Sánchez, L. et al., "Gelatinized/freeze-dried starch as excipient in sustained release tablets," International Journal of Pharmaceutics, 1995, 115, 201-208.
Nakano, M. et al., "Preparation and Evaluation of Sustained Release Tablets Prepared with α-Starch," Chem. Pharm. Bull., 1987, 35, 4345-4350.
Rak, J. et al., "Modified starches—new auxiliary substances in the production of tablets," *Acta Facultatis Pharmaceuticae*, Tom. XXXVII, pp. 5-27, 1983.
Bühler, V. et al., "Generic Drug Formulations," Fine Chemicals, $2^{nd}$ edition 1998, Tetrazepam Tablets (50 mg.).
International Search report dated Jul. 13, 2000, for related International Application No. PCT/EP00/02620.
Bottenbert, P. et al., "Development and Testing of Bioadhesive, Fluoride-Containing slow Release Tablets for Oral Use, Part I: In Vitro and In Vivo Broadhesion," Proceed. Intern. Symp. Control. Rel. Bioact. Mater., 18 (1991), pp. 631-632.

\* cited by examiner

*Primary Examiner* — Michael G Hartley
*Assistant Examiner* — Micah-Paul Young
(74) *Attorney, Agent, or Firm* — Kiera K. Mathey

(57) ABSTRACT

The present invention concerns the use of pregelatinized starch to prevent dose-dumping from a hydrophilic controlled release formulation. It also concerns a hydrophilic controlled release formulation, more in particular a hydrophilic controlled release matrix formulation, and solid dosage forms prepared therefrom, preferably for once daily oral administration. The hydrophilic controlled release formulation comprises pregelatinized starch, one or more active ingredients, one or more viscous hydrophilic polymers and optionally pharmaceutically acceptable formulating agents. Preferred hydrophilic polymers include hydroxypropyl cellulose and hydroxypropyl methylcellulose.

14 Claims, No Drawings

PREGELATINIZED STARCH IN A CONTROLLED RELEASE FORMULATION

This application is a continuation of U.S. application Ser. No. 10/674,701, filed Sep. 30, 2003, which is a continuation of U.S. Pat. No. 6,667,060, the entireties of which are incorporated by reference.

The present invention concerns the use of pregelatinized starch to prevent dose-dumping from a hydrophilic controlled release formulation. It also concerns a hydrophilic controlled release formulation, more in particular a hydrophilic controlled release matrix formulation, and solid dosage forms prepared therefrom, preferably for once daily oral administration. The hydrophilic controlled release formulation comprises pregelatinized starch, one or more active ingredients, one or more viscous hydrophilic polymers and optionally pharmaceutically acceptable formulating agents. Preferred hydrophilic polymers include hydroxypropyl cellulose and hydroxypropyl methylcellulose.

WO 96/14070 discloses an extended release formulation for oral administration comprising cisapride-(L)-tartrate as the active ingredient embedded in a matrix of two hydrophilic viscous polymers, in particular hydroxypropyl cellulose and hydroxypropyl methylcellulose. These hydrophilic polymers swell upon contact with water, thereby forming a gellayer from which the active ingredient is gradually released.

WO 97/24109 describes bioadhesive pharmaceutical compositions and solid dosage forms prepared therefrom, which comprise a pharmaceutically effective amount of an active ingredient, from 80% to 98% (w/w) pregelatinized starch incorporated in the composition as a bioadhesive polymer, and from 1% to 10% (w/w) of a hydrophilic matrix forming polymer. Said dosage forms have a regular and prolonged release pattern for a locally acting ingredient or also for a systemically acting drug, and they are suitable for oral, nasal, rectal and vaginal administration.

EP 0299877 concerns a tablet containing salbutamol or a derivative thereof homogeneously dispersed in a hydrophilic matrix comprising at least one high molecular weight cellulose hydrocolloid as swelling agent, in particular hydroxypropyl methylcellulose 15 Pa·s, and a diluent, in which said diluent comprises one intrinsic diluent and one thickening diluent, in particular pregelatinized maize starch.

EP 0280613 describes a tablet comprising a homogeneous dispersion of dihydroergotamine or one of its derivatives in a water-soluble matrix comprising one or more water-soluble polymeric substances, in particular hydroxypropyl methylcellulose, and a diluent comprising at least one starch derivative, in particular pregelatinized maize starch.

EP 0477061 claims a sustained-release tablet comprising isosorbide 5-mononitrate in homogeneous dispersion in a hydrophilic matrix based on at least one swelling component, in particular hydroxypropyl methylcellulose, and at least one diluent. The latter contains at least one intrinsic diluent and one thickening diluent chosen from polymers such as starch and starch derivatives.

GB 2,195,893 describes a sustained release pharmaceutical composition comprising a pharmacologically active agent in admixture with a) microcrystalline cellulose and b) hydroxypropyl methylcellulose wherein the weight ratio of a) to b) is at least 1 to 1, with the proviso that when the active ingredient is other than acetyl salicylic acid in free form or salt form, the active agent is also in admixture with pregelatinized starch.

WO 97/04752 describes a pharmaceutical composition for oral administration of conjugated estrogens. Said conjugated estrogens are coated onto one or more organic excipients comprising hydroxypropyl methylcellulose and pregelatinized starch, the latter being present as a suitable binder.

Controlled release pharmaceutical preparations regulate the release of the incorporated active ingredient or ingredients over time and comprise preparations with a prolonged, a sustained, a slow, a continuous, a retarded or an extended release, so they accomplish therapeutic or convenience objectives not offered by conventional dosage forms such as solutions or promptly dissolving dosage forms. Controlled release of active ingredient(s) allows to simplify the patient's posological scheme by reducing the amount of recommended daily intakes and improves patient's compliance. One should not underestimate the positive psychological effect towards the patient of a once daily intake instead of a twice or multiple daily intake.

A controlled release of active ingredient(s) from a pharmaceutical preparation may be accomplished by homogeneously embedding said active ingredient(s) in a hydrophilic matrix, being a soluble, partially soluble or insoluble network of viscous, hydrophilic polymers, held together by physical or chemical entanglements, by ionic or crystalline interactions, by complex formation, by hydrogen bonds or van der Waals forces. Said hydrophilic matrix swells upon contact with water, thereby creating a protective gellayer from which the active ingredient(s) is (are) slowly, gradually, continuously released in time either by diffusion through the polymeric network, by erosion of the gellayer, by dissolution of the polymer, or by a combination of said release mechanisms. Commonly used hydrophilic polymers for the preparation of controlled release matrices comprise polysaccharides, polyacrylates, and polyalkylene oxides.

An effective oral controlled release preparation, especially a once or twice daily controlled release preparation, preferably retains its pharmacokinetic release profile along its way through the gastro-intestinal tract so as to avoid undesirable fluctuations in drug plasma concentrations or complete dose-dumping. This implies that a controlled release preparation preferably has to provide a controlled release profile and in particular has to avoid dose-dumping in media of varying ionic strength since the gastro-intestinal luminal content exhibits varying values of ionic strength in different regions of the gastro-intestinal tract.

When administering a controlled release preparation to patients in the fed state, food related dose-dumping may be encountered. The problem of food related dose-dumping in fed patients can be attributed to a lot of factors. One of these factors is surely the mechanical forces that are exerted by the stomach on its content and thus on an ingested preparation. Another factor appears to be the ionic strength of the gastro-intestinal juices. Since the ionic strength values encountered in the gastro-intestinal tract vary not only with the region of the tract, but also with the intake of food, a controlled release formulation preferably also has to provide a controlled release profile and in particular has to avoid dose-dumping regardless whether the patient is in fasted or fed conditions. The ionic strength of the gastro-intestinal fluids may range from about 0.01 to about 0.2 (Johnson et al., 1993, Int. J. Pharm., 90, 151-159).

The ionic strength, mostly represented by the symbol p (sometimes I), is a characteristic of a solution and is defined as $$\mu = 1/2 \sum_i c_i \cdot Z_i^2$$

wherein $c_i$ is the molar concentration of the ith ion, $Z_i$ is its charge, and the summation extends over all the ions in solution (Martin, A., 1993, Physical Pharmacy, Williams & Wilkins, pp 134-135). The ionic strength is thus a property of the solution and not of any particular ion in the solution. The ionic strength is known to constitute a good measure of the non-ideality imposed by all the ions of a solution on the ions produced by a given electrolyte in the solution.

The effect of the ionic strength of the surrounding medium on the disintegration, gelation and viscosity of hydrophilic matrices is described in the literature.

Mitchell et al. (Pharmaceutical Technology. Controlled drug release, vol. 2, by Wells, J. I., Rubinstein, M. H. (Eds.), Ellis Horwood Limited, pp. 23-33, 1991) disclose the effect of electrolytes on the disintegration and gelation of hydroxypropyl methylcellulose (HPMC) K15M matrix tablets. At low ionic strength of the surrounding medium, HPMC matrices are unaffected by electrolytes and hydration occurs to produce an intact gel layer. At intermediate ionic strength however, the matrices lose shape and integrity, and they disintegrate rapidly. The tablets cease to act as controlled release matrices because gelation is prevented by a reduction in hydration in case of increased solute concentrations in the surrounding medium. Thus, electrolytes present in the surrounding medium can modify the release profile of drugs from HPMC matrices. The drugs themselves may also influence the hydration, and thus the gelation of HPMC. Therefore, drugs may play an active role in determining their own release (Mitchell et al., Int. J. Pharm., 1993, 100, 165-173). Consequently, the incorporation of drugs in HPMC matrices may result in unpredictable dissolution profiles and hence unpredictable therapeutic efficiency of the dosage forms.

The swelling behaviour of xanthan gum matrix tablets in sodium chloride solutions of different ionic strength is described in Int. J. Pharm., 1995, 120, 63-72. Within the range of physiological ionic strength, the swelling of the xanthan gum tablets shows a reciprocal relationship with salt concentration.

Unexpectedly, it has been found that the impairing or even destroying effect of the ionic strength of a release medium on the controlled release profile of a hydrophilic matrix formulation can be countered by adding pregelatinized starch to the formulation. Said impairing effect of ionic strength on the controlled release profile of a hydrophilic matrix formulation may be attributed, as indicated hereinbefore, to changes in the hydration of the viscous hydrophilic matrix polymers. Said matrix polymers have to compete for hydration water with the solutes making up the ionic strength of the release medium. Consequently, the polymers may not hydrate to such extent as to ensure formation of a sufficiently integer matrix with acceptable resistance to disintegration. Hydration of the matrix polymers may largely or even completely be suppressed so that the matrix disintegrates almost immediately, e.g. within a time interval of 15 min after administration in the release medium. By incorporating pregelatinized starch in the formulation, the controlled release of active ingredient(s) from a hydrophilic controlled release formulation can be safeguarded or maintained in release media of changing ionic strength, in particular in release media with increasing ionic strength, more in particular in release media with ionic strength values ranging up to 0.4, even more in particular in release media with ionic strength values encountered in physiological conditions, i.e. along the entire gastro-intestinal tract both in fasted as well as in fed conditions, and most in particular in release media with ionic strength values ranging from about 0.01 to about 0.2.

Thus, the present invention relates to the use of pregelatinized starch in a hydrophilic controlled release formulation comprising one or more active ingredients and one or more viscous hydrophilic polymers to counter the impairing effect of ionic strength of the release medium on the controlled release of active ingredient(s) from said formulation or the use of pregelatinized starch in a hydrophilic controlled release formulation comprising one or more active ingredients and one or more viscous hydrophilic polymers to maintain a controlled release of active ingredient(s) from said formulation in release media with changing ionic strength, in particular in release media with increasing ionic strength, more in particular in release media with ionic strength values ranging up to 0.4, even more in particular in release media with ionic strength values encountered in physiological conditions, i.e. along the entire gastro-intestinal tract both in fasted as well as in fed conditions, and most in particular in release media with ionic strength values ranging from about 0.01 to about 0.2. This invention also includes the use of pregelatinized starch in a hydrophilic controlled release formulation comprising one or more active ingredients and one or more viscous hydrophilic polymers to prevent dose-dumping from said formulation along the gastro-intestinal tract both in fasted as well as in fed conditions, more in particular to prevent food-related dose-dumping.

The term "release medium" as used hereinbefore or hereinafter encompasses all kinds of liquid media wherein the release of active ingredient(s) from the hydrophilic controlled release formulation can occur, i.e. for example in in vitro dissolution media, but also in body fluids, more in particular in the gastro-intestinal fluids.

The term "to maintain a controlled release of active ingredient(s) from the formulation" indicates that the active ingredient(s) is (are) slowly, gradually, continuously, prolonged, sustained or extended released in time from the formulation. In particular, the term "a controlled release of active ingredient(s) from the formulation" indicates that the formulation does not release the active ingredient immediately after oral dosing and that the formulation allows a reduction in dosage frequency, following the definition for extended release, interchangeable with controlled release, according to the United States Pharmacopeia 24, p 2059. A controlled release, used synonymously with prolonged action, sustained release, or extended release, dosage form is therein described as a dosage form that allows at least a two-fold reduction in dosing frequency or a significant increase in patient compliance or therapeutic performance as compared to that presented as a conventional dosage form (e.g. as a solution or a prompt drug-releasing, conventional solid dosage form).

The term "dose-dumping" is well known by a person skilled in the art and defines a sudden release of a major part or all of the active ingredient(s) incorporated in a formulation intended to be used as a controlled release formulation. Instead of a release spread over an extended period of time, the whole dose or at least a major part thereof is released within a short period of time. This may cause serious adverse effects or even death depending on the active ingredient and potency thereof.

The present invention also relates to a hydrophilic controlled release formulation comprising pregelatinized starch, one or more active ingredients, one or more viscous hydrophilic polymers and optionally pharmaceutically acceptable formulating agents characterized in that the pregelatinized starch enables the formulation to maintain a controlled release of the incorporated active ingredient(s) in release media with changing ionic strength, in particular in release media with increasing ionic strength, more in particular in release media with ionic strength values ranging up to 0.4, even more in particular in release media with ionic strength values encountered in physiological conditions, i.e. along the entire gastro-intestinal tract both in fasted as well as in fed conditions, and most in particular in release media with ionic strength values ranging from about 0.01 to about 0.2. The invention also concerns a hydrophilic controlled release formulation comprising pregelatinized starch, one or more active ingredients, one or more viscous hydrophilic polymers and optionally pharmaceutically acceptable formulating agents characterized in that the pregelatinized starch prevents dose-dumping from said formulation along the gastro-intestinal tract both in fasted as well as in fed conditions, more in particular the pregelatinized starch prevents food-related dose-dumping.

The formulation according to the present invention is particularly useful for administering one or more active ingredients (a) with a short half-life, in the order of 4 to 8 hours or less, which have to be taken in divided doses during the day when administered in a conventional preparation; or
(b) with a narrow therapeutic index; or
(c) with sufficient absorption over the entire gastro-intestinal tract; or
(d) with a relatively small therapeutically effective dose.

Suitable active ingredients are those which exert a local physiological effect, as well as those which exert a systemic effect, after oral administration. Examples thereof are:

analgesic and anti-inflammatory drugs (NSAIDs, fentanyl, indomethacin, ibuprofen, ketoprofen, nabumetone, paracetamol, piroxicam, tramadol, COX-2 inhibitors such as celecoxib and rofecoxib);

anti-arrhythmic drugs (procainamide, quinidine, verapamil);

antibacterial and antiprotozoal agents (amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, norfloxacin, ofloxacin, oxacillin, phenoxymethylpenicillin potassium, pyrimethamine-sulfadoxime, streptomycin);

anti-coagulants (warfarin);

antidepressants (amitriptyline, amoxapine, butriptyline, clomipramine, desipramine, dothiepin, doxepin, fluoxetine, reboxetine, amineptine, selegiline, gepirone, imipramine, lithium carbonate, mianserin, milnacipran, nortriptyline, paroxetine, sertraline; 3-[2-[3,4-dihydrobenzofuro[3,2-c]pyridin-2(1H)-yl]ethyl]-2-methyl-4H-pyrido[1,2-a]pyrimidin-4-one);

anti-diabetic drugs (glibenclamide, metformin);

anti-epileptic drugs (carbamazepine, clonazepam, ethosuximide, gabapentin, lamotrigine, levetiracetam, phenobarbitone, phenyloin, primidone, tiagabine, topiramate, valpromide, vigabatrin);

antifungal agents (amphotericin, clotrimazole, econazole, fluconazole, flucytosine, griseofulvin, itraconazole, ketoconazole, miconazole nitrate, nystatin, terbinafine, voriconazole);

antihistamines (astemizole, cinnarizine, cyproheptadine, decarboethoxyloratadine, fexofenadine, flunarizine, levocabastine, loratadine, norastemizole, oxatomide, promethazine, terfenadine);

anti-hypertensive drugs (captopril, enalapril, ketanserin, lisinopril, minoxidil, prazosin, ramipril, reserpine, terazosin);

anti-muscarinic agents (atropine sulphate, hyoscine);

antineoplastic agents and antimetabolites (platinum compounds, such as cisplatin, carboplatin; taxanes, such as paclitaxel, docetaxel; tecans, such as camptothecin, irinotecan, topotecan; vinca alkaloids, such as vinblastine, vindecine, vincristine, vinorelbine; nucleoside derivatives and folic acid antagonists such as 5-fluorouracil, capecitabine, gemcitabine, mercaptopurine, thioguanine, cladribine, methotrexate; alkylating agents, such as the nitrogen mustards, e.g. cyclophosphamide, chlorambucil, chlormethine, iphosphamide, melphalan, or the nitrosoureas, e.g. carmustine, lomustine, or other alkylating agents, e.g. busulphan, dacarbazine, procarbazine, thiotepa; antibiotics, such as daunorubicin, doxorubicin, idarubicin, epirubicin, bleomycin, dactinomycin, mitomycin; HER 2antibody, such as trastuzumab; podophyllotoxin derivatives, such as etoposide, teniposide; farnesyl transferase inhibitors; anthrachinon derivatives, such as mitoxantron);

anti-migraine drugs (alniditan, naratriptan, sumatriptan);

anti-Parkinsonian drugs (bromocryptine mesylate, levodopa, selegiline);

antipsychotic, hypnotic and sedating agents (alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone, zolpidem);

anti-stroke agents (lubeluzole, lubeluzole oxide, riluzole, aptiganel, eliprodil, remacemide)

antitussive (dextromethorphan, laevodropropizine);

antivirals (acyclovir, ganciclovir, loviride, tivirapine, zidovudine, lamivudine, zidovudine+lamivudine, didanosine, zalcitabine, stavudine, abacavir, lopinavir, amprenavir, nevirapine, efavirenz, delavirdine, indinavir, nelfinavir, ritonavir, saquinavir, adefovir, hydroxyurea);

beta-adrenoceptor blocking agents (atenolol, carvedilol, metoprolol, nebivolol, propanolol);

cardiac inotropic agents (aminone, digitoxin, digoxin, milrinone);

corticosteroids (beclomethasone dipropionate, betamethasone, budesonide, dexamethasone, hydrocortisone, methylprednisolone, prednisolone, prednisone, triamcinolone);

disinfectants (chlorhexidine);

diuretics (acetazolamide, frusemide, hydrochlorothiazide, isosorbide)

enzymes;

essential oils (anethole, anise oil, caraway, cardamom, cassia oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol, thyme)

gastro-intestinal agents (cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel, sulphasalazine);

haemostatics (aminocaproic acid);

lipid regulating agents (atorvastatin, lovastatin, pravastatin, probucol, simvastatin);
local anaesthetics (benzocaine, lignocaine);
opioid analgesics (buprenorphine, codeine, dextromoramide, dihydrocodeine, hydrocodone, oxycodone, morphine);
parasympathomimetics and anti-dementia drugs (AIT-082, eptastigmine, galanthamine, metrifonate, milameline, neostigmine, physostigmine, tacrine, donepezil, rivastigmine, sabcomeline, talsaclidine, xanomeline, memantine, lazabemide);
peptides and proteins (antibodies, becaplermin, cyclosporine, erythropoietin, immunoglobulins, insuline);
sex hormones (oestrogens: conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxy-progesterone acetate, megestrol, norethindrone, norethindrone acetate, norethisterone, norethisterone acetate, norethynodrel, norgestimate, norgestrel, norgestrienone, progesterone, quingestanol acetate)
stimulating agents (sildenafil);
vasodilators (amlodipine, buflomedil, amyl nitrite, diltiazem, dipyridamole, glyceryl trinitrate, isosorbide dinitrate, lidoflazine, molsidomine, nicardipine, nifedipine, oxpentifylline, pentaerythritol tetranitrate);
their N-oxides, their pharmaceutically acceptable acid or base addition salts and their stereochemically isomeric forms.

Pharmaceutically acceptable acid addition salts comprise the acid addition salt forms which can conveniently be obtained by treating the base form of the active ingredient with appropriate organic and anorganic acids.

Active ingredients containing an acidic proton may be converted into their non-toxic metal or amine addition salt forms by treatment with appropriate organic and inorganic bases.

The term addition salt also comprises the hydrates and solvent addition forms which the active ingredients are able to form. Examples of such forms are e.g. hydrates, alcoholates and the like.

The N-oxide forms of the active ingredients comprise those active ingredients wherein one or several nitrogen atoms are oxidized to the so-called N-oxide.

The term "stereochemically isomeric forms" defines all the possible stereoisomeric forms which the active ingredients may possess. More in particular, stereogenic centers may have the R- or S-configuration, and active ingredients containing one or more double bonds may have the E- or Z-configuration.

An interesting group of active ingredients are those as described hereinabove provided that salbutamol, isosorbide 5-mononitrate, dihydroergotamine, vitamin B12, conjugated estrogens, acetyl salicylic acid, fluoride, miconazole and triamcinolone are not included.

Another interesting group of active ingredients are those as described hereinabove provided that salbutamol, isosorbide 5-mononitrate, dihydroergotamine, vitamin B12, conjugated estrogens, acetyl salicylic acid, fluoride, miconazole, triamcinolone, acyclovir, lamotrigine and acetaminophen in combination with diphenhydramine are not included.

In view of the presence of one or more active ingredients, the present invention also relates to a hydrophilic controlled release formulation as described hereinabove for use as a medicine.

As described hereinabove, pregelatinized starch is comprised in the present formulation. Pregelatinized starch is a readily available product, which can be manufactured by precooking and drying starches. It is widely used in the food industry in order to give viscous pastes after reconstitution in water.

Pregelatinization may be obtained by:
spray drying: pregelatinized starches produced in this way consist of hollow spheres, usually with an air cell enclosed at the center. They are made by first cooking the starch in water and then by spraying the hot paste into a drying chamber or tower;
roll-drying: pregelatinized starches prepared in this way consist of particles appearing as transparent, flat irregular platelets. In general these products are simultaneously cooked and dried on heated rolls, using either a closely set pair of squeeze rolls or a single roll with a closely set doctor blade. In either case, a paper thin flake, which is then ground to mesh size, is obtained;
extrusion or drum-drying: pregelatinized starches prepared in this way consist of individual particles which are much thicker and more irregular than roll-dried products. Drum-drying is similar to roll-drying except that a thicker coating of starch paste is applied to the heated rolls, and the dried product is then ground to the desired particle size. In the extrusion process, moistened starch is forced through a super heated chamber under very high shear, then exploded and simultaneously dried by venting at atmospheric pressure.

A preferred form of pregelatinized starch is drum dried waxy maize starch, which is available from the company Cerestar Benelux BV (Breda, the Netherlands).

The weight percentage of pregelatinized starch in the hydrophilic controlled release formulation of the present invention preferably ranges from about 0.01% to less than 80% (w/w), more preferably from about 0.01% to about 15%, even more preferably from about 0.01% to about 5%, and most preferred is about 5%.

The hydrophilic polymers constituting the controlled release matrix preferably release the active ingredient(s) gradually, slowly, continuously. They swell upon contact with aqueous fluid following administration, resulting in a viscous, drug release regulating gellayer. The viscosity of the polymers preferably ranges from 150 to 100,000 mPa·s (apparent viscosity of a 2% aqueous solution at 20° C.).
Examples of such polymers are
alkylcelluloses, such as, methylcellulose;
hydroxyalkylcelluloses, for example, hydroxymethylcellulose, hydroxyethylcellulose, hydroxypropylcellulose and hydroxybutylcellulose;
hydroxyalkyl alkylcelluloses, such as, hydroxyethyl methylcellulose and hydroxypropyl methylcellulose;
carboxyalkylcelluloses, such as, carboxymethylcellulose;
alkali metal salts of carboxyalkylcelluloses, such as, sodium carboxymethylcellulose;
carboxyalkylalkylcelluloses, such as, carboxymethylethylcellulose;
carboxyalkylcellulose esters;
other natural, semi-synthetic, or synthetic polysaccharides, such as, alginic acid, alkali metal and ammonium salts thereof, carrageenans, galactomannans, tragacanth, agar-agar, gummi arabicum, guar gummi, xanthan gummi, starches, pectins, such as sodium carboxymethylamylopectin, chitin derivates such as chitosan, polyfructans, inulin;
polyacrylic acids and the salts thereof, polymethacrylic acids and the salts thereof, methacrylate copolymers;
polyvinylalcohol;
polyvinylpyrrolidone, copolymers of polyvinylpyrrolidone with vinyl acetate;
combinations of polyvinylalcohol and polyvinylpyrrolidone;
polyalkylene oxides such as polyethylene oxide and polypropylene oxide and copolymers of ethylene oxide and propylene oxide.

Preferable hydrophilic polymers are polysaccharides, more in particular cellulose derivatives and most in particular cellulose ether derivatives.

Most preferred cellulose ether derivatives are hydroxypropyl methylcellulose and hydroxypropyl cellulose.

Different viscosity grades of hydroxypropyl cellulose and hydroxypropyl methylcellulose are commercially available.

Hydroxypropyl methylcellulose preferably used in the present invention has a viscosity grade ranging from about 3,500 mPa·s to about 100,000 mPa·s, in particular ranging from about 4,000 mPa·s to about 20,000 mPa·s and most in particular a viscosity grade of about 6,500 mPa·s to about 15,000 mPa·s (apparent viscosity of a 2% aqueous solution at 20° C.), e.g. hypromellose 2208 (DOW, Antwerp, Belgium).

Hydroxypropyl cellulose having a viscosity lower than 1,500 mPa·s (apparent viscosity of a 2% aqueous solution at 20° C.) is preferred, in particular hydroxypropyl cellulose having a viscosity in the range from about 150 to about 700 mPa·s, preferably from 200 to 600 mPa·s, e.g. Klucel EF® (Hercules, Wilminton, USA).

The viscous hydrophilic polymers constituting the matrix mainly provide for the controlled pharmacokinetic release profile of the preparation. Depending on the amount of polymers processed in the preparation, the release profile can be tuned. Preferably, the amount of viscous hydrophilic polymer in the present formulation ranges from about 0.01 to about 80% (w/w). In addition, when using a combination of polymers, the ratio of said polymers also influences the release profile of the preparation. For example, when using one or more hydrophilic polymers, preferably cellulose derivatives, more in particular hydroxypropyl cellulose and hydroxypropyl methylcellulose, the weight percentage (% w/w) of hydroxypropyl methylcellulose preferably ranges from 0 to about 16%; the weight percentage of hydroxypropyl cellulose preferably ranges between about 25% and about 62%. The ratio of hydroxypropyl cellulose to hydroxypropyl methylcellulose preferably ranges from 1:5 to 5:1, more preferable from 1:1 to 5:1, and most preferred from 3:1 to 5:1.

A combination of different polymers offers the possibility of combining different mechanisms by which the active ingredient(s) is (are) released from the matrix. Such combination facilitates control of the pharmacokinetic release profile of the preparation at will. As mentioned hereinabove, three main mechanisms exist by which an active ingredient can be released from a hydrophilic matrix: dissolution, erosion and diffusion. An active ingredient will be released by the dissolution mechanism when it is homogeneously dispersed in a matrix network of a soluble polymer. The network will gradually dissolve in the gastro-intestinal tract, thereby gradually releasing its load. The matrix polymer can also gradually be eroded from the matrix surface, likewise releasing the active ingredient in time. When an active ingredient is processed in a matrix made up of an insoluble polymer, it will be released by diffusion: the gastro-intestinal fluids penetrate the insoluble, sponge-like matrix and diffuse back out loaded with drug. Release of one or more active ingredients from a matrix containing hydroxypropyl cellulose and hydroxypropyl methylcellulose occurs by a combined set of release mechanisms. Due to the higher solubility of hydroxypropyl methylcellulose compared with hydroxypropyl cellulose, the former will gradually dissolve and erode from the matrix, whereas the latter will more act as a sponge-like matrix former releasing the active ingredient mainly by diffusion.

Beside active ingredient(s), hydrophilic polymers and pregelatinized starch, the formulation of the present invention may also optionally comprise pharmaceutically acceptable formulating agents in order to promote the manufacture, compressibility, appearance and taste of the preparation. These formulating agents comprise, for example, diluents or fillers, glidants, binding agents, granulating agents, anti-caking agents, lubricants, flavors, dyes and preservatives.

The filler may be selected from soluble fillers, for example, sucrose, lactose, trehalose, maltose, mannitol, sorbitol, inulin, and from insoluble fillers, for example, dicalcium or tricalcium phosphate, talc. An interesting filler is lactose, in particular, lactose monohydrate. Different grades of lactose can be used. One type of lactose preferably used in the present invention is lactose monohydrate 200 mesh (DMV, Veghel, the Netherlands). Another lactose monohydrate, lactose monohydrate of the type DCL 11 (DMV, Veghel, the Netherlands), can also preferably be used. The notation DCL refers to "Direct Compression Lactose". The number 11 is a reference number of the manufacturer. This type of lactose is characterised in that 98% (w/w) of the particles have a diameter smaller than 250 µm, 30% (w/w) to 60% (w/w) of the particles have a diameter of 100 µm and at maximum 15% (w/w) of the particles have a diameter of smaller than 45 µm.

The weight percentage of filler ranges between about 6% and about 54% (w/w).

Among the optional formulating agents that further may be comprised in the matrix formulation there may be mentioned agents such as polyvidone; starch; acacia gum; gelatin; seaweed derivatives, e.g. alginic acid, sodium and calcium alginate; cellulose derivatives, e.g. ethylcellulose, hydroxypropylmethylcellulose, having useful binding and granulating properties; glidants such as colloidal silica, starch or talc; lubricants such as magnesium stearate and/or palmitate, calcium stearate, stearic acid, polyethylene glycol, liquid paraffin, sodium or magnesium lauryl sulphate; antiadherents such as talc and corn starch.

In addition to the pharmaceutical acceptable formulating agents described above, cyclodextrins or derivatives thereof may also be included in the present controlled release formulation to improve the dissolution rate of the active ingredient(s). For this purpose, the recommended amount of cyclodextrin or derivatives thereof may replace an equivalent amount of filler. Drug release from an oral solid controlled release dosage form and subsequent absorption of the drug from the gastro-intestinal tract into the blood stream is dissolution-rate dependent and can be slow and irregular especially in case of a sparingly water soluble, a slightly water soluble, a very slightly water soluble, a practically water insoluble or a water insoluble drug, defined according to the United States Pharmacopeia 24, p 10.

In case of a drug with a pH dependent solubility, the release of the drug from the dosage form and subsequent the absorption into the blood stream can vary during the passage of the dosage form along the gastro-intestinal tract. This is especially relevant for an alkaline drug exhibiting a decreasing solubility with increasing pH. When passing along the gastro-intestinal tract, the controlled release formulation will reside for a substantial period of time in the lower part of the tract (ileum and colon) where the average pH value of the luminal content varies from 7.5 (ileum) over 6.4 (right colon) to 7.0

(left colon) (Evans et al., Gut, 29, 1035-1041, 1988; Wilson and Washington, in Physiological Pharmaceutics, Ellis Horwood Limited, West Sussex, UK, pp. 21-36, 1989). This higher pH value in the lower part of the gastro-intestinal tract, when compared with the upper part, may cause a decrease in solubility of the alkaline drug resulting in a lower drug release from the dosage form and hence a lower and slower drug absorption.

Cyclodextrins or derivatives thereof are generally known as complexing agents. By incorporating a drug/cyclodextrin complex into the controlled release formulation of the present invention, the dissolution rate and subsequently the absorption characteristics of sparingly water soluble, slightly water soluble, very slightly water soluble, practically water insoluble or water insoluble drugs or drugs having a pH dependent solubility can be improved. In particular, it provides for a faster or more regular release of said drugs; preferably a zero-order release is obtained. Beside the dissolution-rate enhancing function, the cyclodextrin or derivatives thereof may also act as an eroding element of the present formulation.

The cyclodextrin to be used in the present invention includes the pharmaceutically acceptable unsubstituted and substituted cyclodextrins known in the art, more particularly α, β or γ cyclodextrins or the pharmaceutically acceptable derivatives thereof.

Substituted cyclodextrins which can be used in the invention include polyethers described in U.S. Pat. No. 3,459,731. In general, unsubstituted cyclodextrins are reacted with an alkylene oxide, preferably under superatmospheric pressure and at an elevated temperature, in the presence of an alkaline catalyst.

Since a hydroxy moiety of the cyclodextrin can be substituted by an alkylene oxide which itself can react with yet another molecule of alkylene oxide, the average molar substitution (MS) is used as a measure of the average number of moles of the substituting agent per glucose unit. The MS can be greater than 3 and theoretically has no limit.

Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or, more in particular, by methyl, ethyl, hydroxyethyl, hydroxypropyl, hydroxybutyl, carboxymethyl or carboxyethyl.

In the foregoing definitions the term "$C_{1-2}$alkyl" is meant to include saturated hydrocarbon radicals having 1 or 2 carbon atoms, such as methyl or ethyl; the term "$C_{1-3}$alkyl" is meant to include straight and branched chain saturated hydrocarbon radicals, having from 1 to 3 carbon atoms, including those described for the term "$C_{1-2}$alkyl" and 1-methylethyl, propyl; the term "$C_{2-4}$alkyl" is meant to include straight and branched chain saturated hydrocarbon radicals, having from 2 to 4 carbon atoms, including ethyl, 1-methylethyl, 1,1-dimethylethyl, propyl, 2-methylpropyl, butyl, and the like; the term "$C_{1-6}$alkyl" is meant to include straight and branched chain saturated hydrocarbon radicals, having from 1 to 6 carbon atoms, including those described for the terms mentioned hereinbefore and pentyl, hexyl and the like.

Such ethers can be prepared by reacting the starting cyclodextrin with an appropriate O-alkylating agent or a mixture of such agents in a concentration being selected so that the desired cyclodextrin ether is obtained. The said reaction is preferably conducted in a suitable solvent in the presence of an appropriate base. With such ethers, the degree of substitution (DS) is the average number of substituted hydroxy functions per glucose unit, the DS being thus 3 or less.

In the cyclodextrin derivatives for use in the formulation according to the present invention, the DS preferably is in the range of 0.125 to 3, in particular 0.3 to 2, more in particular 0.3 to 1 and the MS is in the range of 0.125 to 10, in particular of 0.3 to 3 and more in particular 0.3 to 1.5.

Of particular utility in the present invention are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another suitable type of substituted cyclodextrins is sulfobutylcyclodextrins. This type is also envisaged in the present invention.

The cyclodextrin preferably being used in the present invention is β-cyclodextrin, and more in particular hydroxypropyl β-cyclodextrin, because of its higher water solubility.

The ratio of cyclodextrin over active ingredient may vary widely. It depends on the active ingredient or the cyclodextrin being used, the desired dissolution profile, the solubility of the cyclodextrin and active ingredient in the solvent used to prepare the cyclodextrin-active ingredient mixture, as described hereinafter. Preferably, ratio's of at least 1:1 may be applied, although lower ratio's are not excluded.

The use of a mixture of cyclodextrins, either different types (α, β, γ) or different substitutions (2-hydroxypropyl or methyl) or different substitution grades is also envisaged in the present invention.

To incorporate the cyclodextrins or derivatives thereof in the present controlled release formulation, the cyclodextrin is preferably first intimately mixed with the active ingredient(s), followed by mixing this intimate mixture with the remaining components of the controlled release formulation.

Different techniques can be used to prepare the intimate mixture of the cyclodextrin and the active ingredient(s), comprising a) a simple mixing technique wherein the two components are physically mixed in a suitable mixing apparatus, e.g. a Turbula mixer (Willy A. Bachoven Machinenfabrik, Bazel, Swiss);

b) a ball-milling technique wherein the two components are brought together and milled in a suitable ball-mill (Retsch GMBH & Co, Haan, Germany);

c) a dry compaction technique wherein the cyclodextrin and the active ingredient(s) are mixed in a suitable mixing apparatus. The resulting mixture is then run through a compactor, e.g. a Polygran 3W compactor (Gerteis, Jona, Swiss), followed by breaking down the resulting agglomerates, e.g. sheets or plates.

d) a solid dispersion technique. The term "a solid dispersion" used hereinafter defines a system in a solid state (as opposed to a liquid or gaseous state) comprising at least two components, in casu the active ingredient(s) and the cyclodextrin, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution" hereinafter. Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline active ingredient(s), or amorphous, microcrystalline or crystalline cyclodextrin, or both, are dispersed more or less evenly in another phase comprising cyclodextrin, or active ingredient(s), or a solid solution comprising active ingredient(s) and cyclodextrin. Said domains are regions within the solid dispersion distinctively marked by some physical feature, small in size, and evenly and randomly distributed throughout the solid dispersion.

Various techniques exist for preparing solid dispersions including melt-extrusion, spray-drying, freeze-drying and solution-evaporation, the latter technique being preferred.

The solution-evaporation process comprises the following steps:
a) dissolving the active ingredient(s) and the cyclodextrin in an appropriate solvent, such as water or an organic solvent, such as an alcohol, e.g. methanol, ethanol, or mixtures thereof, optionally at elevated temperatures;
b) evaporating the solvent of the solution resulting under point a), optionally under vacuum. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

In the freeze-drying technique, the cyclodextrin and the active ingredient(s) are dissolved in an appropriate solvent. This mixture is then frozen followed by sublimating the solvent under vacuum and under supply of heat of sublimation while continuously removing the vapor formed. The resulting freeze-dried solid may be subjected to a secondary drying process at elevated temperature.

The melt-extrusion process comprises the following steps
a) mixing the active ingredient(s) and the cyclodextrin,
b) optionally blending additives with the thus obtained mixture,
c) heating and compounding the thus obtained blend until one obtains a homogeneous melt,
d) forcing the thus obtained melt through one or more nozzles; and
e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

It will be appreciated that a person of skill in the art will be able to optimize the parameters of the techniques for the preparation of the intimate mixture of active ingredient(s) and cyclodextrin described above, such as the most appropriate solvent, the working temperature, the kind of apparatus being used, the rate of mixing and milling, the rate of spray-drying, the freezing rate, the sublimation rate, the throughput rate in the melt-extruder and the like.

Instead of cyclodextrins or derivatives thereof other water-soluble polymers may be used to prepare the above described intimate mixture with the active ingredient(s). Suitable water-soluble polymers have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, the water-soluble polymer can be selected from the group comprising
alkylcelluloses such as methylcellulose,
hydroxyalkylcelluloses such as hydroxymethylcellulose, hydroxyethylcellulose, hydroxypropylcellulose and hydroxybutylcellulose,
hydroxyalkyl alkylcelluloses such as hydroxyethyl methylcellulose and hydroxypropyl methylcellulose,
carboxyalkylcelluloses such as carboxymethylcellulose,
alkali metal salts of carboxyalkylcelluloses such as sodium carboxymethylcellulose,
carboxyalkylalkylcelluloses such as carboxymethylethylcellulose,
carboxyalkylcellulose esters,
starches,
pectines such as sodium carboxymethylamylopectine,
chitin derivates such as chitosan,
di-, oligo- and polysaccharides such as trehalose, alginic acid, alkali metal and ammonium salts thereof, carrageenans, galactomannans, tragacanth, agar-agar, gummi arabicum, guar gummi and xanthan gummi,
polyacrylic acids and the salts thereof,
polymethacrylic acids, the salts and esters thereof, methacrylate copolymers,
polyvinylalcohol,
polyvinylpyrrolidone, polyvinylpyrrolidone-vinylacetate copolymers,
combinations of polyvinylpyrrolidone and polyvinylalcohol,
polyalkylene oxides such as polyethylene oxide and polypropylene oxide and copolymers of ethylene oxide and propylene oxide.

An interesting formulation according to the present invention is:

| | |
|---|---|
| Active ingredient(s) | 0.01-50% (w/w) |
| Viscous hydrophilic polymer(s) | 0.01-80% (w/w) |
| Pregelatinized starch | 0.01-<80% (w/w) |
| Pharmaceutically acceptable formulating agents | ad 100% (w/w). |
| or | |
| Active ingredient(s) | 0.01-50% (w/w) |
| Viscous hydrophilic polymer(s) comprising hydroxypropyl cellulose | 0.01-80% (w/w) |
| Pregelatinized starch | 0.01-<80% (w/w) |
| Pharmaceutically acceptable formulating agents | ad 100% (w/w). |

Another interesting formulation according to the present invention is:

| | |
|---|---|
| Active ingredient(s) | 0.01-50% (w/w) |
| Viscous hydrophilic polymer(s) | 0.01-80% (w/w) |
| Pregelatinized starch | 0.01-15% (w/w) |
| Pharmaceutically acceptable formulating agents | ad 100% (w/w). |
| or | |
| Active ingredient(s) | 0.01-50% (w/w) |
| Viscous hydrophilic polymer(s) comprising hydroxypropyl cellulose | 0.01-80% (w/w) |
| Pregelatinized starch | 0.01-15% (w/w) |
| Pharmaceutically acceptable formulating agents | ad 100% (w/w). |

Yet another interesting formulation according to the present invention is:

| | |
|---|---|
| Active ingredient(s) | 0.01-50% (w/w) |
| Viscous hydrophilic polymer(s) | 0.01-80% (w/w) |
| Pregelatinized starch | 0.01-5% (w/w) |
| Pharmaceutically acceptable formulating agents | ad 100% (w/w). |
| or | |
| Active ingredient(s) | 0.01-50% (w/w) |
| Viscous hydrophilic polymer(s) comprising hydroxypropyl cellulose | 0.01-80% (w/w) |
| Pregelatinized starch | 0.01-5% (w/w) |
| Pharmaceutically acceptable formulating agents | ad 100% (w/w). |

Still another interesting formulation according to the present invention is:

| | |
|---|---|
| Active ingredient(s) | 0.01-50% (w/w) |
| Hydroxypropyl cellulose | 25-62% (w/w) |
| Hydroxypropyl methylcellulose | 0-16% (w/w) |
| Pregelatinized starch | 0.01 to 5% (w/w) |
| Pharmaceutically acceptable formulating agents | ad 100% (w/w). |

The controlled release matrix formulation of the present invention is generally prepared according to the following process:
(1.a) one or more active ingredients, pregelatinized starch, one or more viscous hydrophilic polymers and optionally some or all of the pharmaceutically acceptable formulating agents are mixed;
(1.b) the powder mixture prepared under (1.a) is run through a compactor, thus yielding plates;
(1.c) the resulting plates are broken down and sieved, thus yielding granules;
(1.d) the resulting granules are optionally mixed with all or the remainder of the pharmaceutically acceptable formulating agents until homogeneous.

In case the active ingredient(s) is a sparingly water soluble, slightly water soluble, very slightly water soluble, practically water insoluble or water insoluble drug or a drug with a pH dependent solubility, in particular an alkaline drug, the active ingredient(s) may be incorporated in the controlled release formulation as an intimate mixture with a cyclodextrin or derivatives thereof or another water soluble polymer, as described hereinabove. In said case, the preparation of the present controlled release formulation comprises an additional first step, namely
(2.a) one or more active ingredients and the water soluble polymer are intimately mixed;
(2.b) the intimate mixture prepared under (2.a) is mixed with pregelatinized starch, one or more viscous hydrophilic polymers and optionally some or all of the pharmaceutically acceptable formulating agents;
(2.c) the powder mixture prepared under (2.b) is run through a compactor, thus yielding plates;
(2.d) the resulting plates are broken down and sieved, thus yielding granules;
(2.e) the resulting granules are optionally mixed with all or the remainder of the pharmaceutically acceptable formulating agents until homogeneous.

The formulation obtained by the processes as described hereinabove may be used for the manufacture of a dosage form, in particular a controlled release dosage form. A preferred dosage form is a solid dosage form, in particular an oral solid dosage form and more in particular a tablet or a capsule, e.g. a capsule filed with pellets obtained from the formulation of the present invention. Said tablet may be obtained by tabletting in an art-known tabletting machine the final blend resulting from the above described processes, i.e. the blend resulting under (1.d) or (2.e).

A compactor as mentioned in step (1.b) or (2.c) of the above described processes is an apparatus wherein the powdery mixture is run between two rollers exerting pressure on the powdery mixture. In this way the mixture is compacted and sheets or plates are formed. Compactors are commercially available, for instance, from the company Gerteis (Jona, Swiss), e.g. a Polygran 3W compactor.

The above general route of preparation of the controlled release formulation may be modified by a person skilled in the art by for instance adding certain ingredients at other stages than indicated above.

As an alternative to the above described route of preparation involving a compaction step, the above described mixture can also be tabletted using direct compression. When using the technique of direct compression, dies or matrices in the form of the desired tablets are filled with a powdery mixture having the tablet composition and then are punched. The advantage of this way of tabletting is that it usually requires less steps. Apparatuses for direct compression tabletting are commercially available. These apparatuses require forced feeding systems whenever the rheological properties of the mixture are not appropriate to fill the dies or matrices without forced feeding.

The resulting tablets may have different kinds of shapes, e.g. oblong or circular. A person skilled in the art will appreciate that the shape of the tablet influences the release period, because of the fact that different shapes have a different ratio of surface to volume. Consequently, in view of the fact that the dissolution of a tablet is a process that mainly takes place at the surface of the tablet, a different shape can mean—but not necessarily—a different dissolution profile.

The resulting tablets may also have different nominal weights and thus different sizes. The size of the tablet affects the surface to volume ratio, and consequently influences the release period, as mentioned hereinabove.

The resulting tablets are manufactured from a homogeneous dispersion of the hereinabove mentioned ingredients. Said dispersion may be obtained by physically mixing the ingredients. The controlled release profile of the tablets is established by the formation of a gellayer due to the swelling of the homogeneously dispersed hydrophilic polymers. This implies that the tablets are dividable and may be provided with a suitable score. This allows one to adjust the recommended dose whenever required.

The above described ingredients, ratios and weight percentages apply for uncoated tablets or for tablet cores, i.e. the tablet without the coating.

However, the tablets of the present invention are preferably film coated with art-known film coating compositions. The coating is applied to improve the aspect and/or the taste of the tablets and the ease with which they can be swallowed. Coating the tablets of the present invention may also serve other purposes, e.g. improving stability and shelf-life.

Suitable coating formulations comprise a film forming polymer such as, for example, hydroxypropyl methylcellulose, e.g. hypromellose 2910 (5 mPa·s), a plasticizer such as, for example, a glycol, e.g. propylene glycol or polyethylene glycol, an opacifier, such as, for example, titanium dioxide, and a film smoothener, such as, for example, talc.

Suitable coating solvents are water as well as organic solvents. Examples of organic solvents are alcohols, e.g. ethanol or isopropanol, ketones, e.g. acetone, or halogenated hydrocarbons, e.g. methylene chloride.

Optionally, the coating may contain a therapeutically effective amount of one or more active ingredients to provide for an immediate release of said active ingredient(s) and thus for an immediate relief of the symptoms treated by said active ingredient(s).

Coated tablets of the present invention are prepared by first making the tablet cores in the way as described above and subsequently coating said tablet cores using conventional techniques, such as coating in a coating pan.

The active ingredient(s) is (are) present in the dosage form prepared from the formulation of the present invention in a therapeutically effective amount. The amount that constitutes a therapeutically effective amount varies according to the ingredients being used, the condition being treated, the severity of said condition, and the patient being treated. The amount of active ingredient(s) used in the present invention preferably ranges between about 0.01% and about 50% (w/w).

The following examples are intended to illustrate the present invention.

EXPERIMENTAL PART

Tablet Formulations

| Tablet 1 | |
|---|---|
| Cisapride-(L)-tartrate | 52.92 mg |
| Lactose monohydrate 200 mesh | 274.83 mg |
| Hydroxypropyl methylcellulose 2208 | 34.2 mg |
| Hydroxypropyl cellulose | 142.5 mg |
| Drum dried waxy maize starch | 28.5 mg |
| Magnesium stearate | 2.85 mg |
| Colloidal anhydrous silica | 5.7 mg |
| Talc* | 28.5 mg |

| Tablet 2 | |
|---|---|
| Cisapride-(L)-tartrate | 52.92 mg |
| Lactose monohydrate 200 mesh | 149.43 mg |
| Hydroxypropyl methylcellulose 2208 | 74.1 mg |
| Hydroxypropyl cellulose | 228.00 mg |
| Drum dried waxy maize starch | 28.5 mg |
| Magnesium stearate | 2.85 mg |
| Colloidal anhydrous silica | 5.7 mg |
| Talc* | 28.5 mg |

| Tablet 3 | |
|---|---|
| 3-[2-[3,4-dihydrobenzofuro[3,2-c]pyridin-2(1H)-yl]ethyl]-2-methyl-4H-pyrido[1,2-a]pyrimidin-4-one microfine | 16.00 mg |
| Lactose monohydrate DCL11 | 108.80 mg |
| Hydroxypropyl methylcellulose 2208 | 41.60 mg |
| Hydroxypropyl cellulose | 128.00 mg |
| Drum dried waxy maize starch | 16.00 mg |
| Magnesium stearate | 6.4 mg |
| Colloidal anhydrous silica | 3.20 mg |

| Tablet 4 | |
|---|---|
| 3-[2-[3,4-dihydrobenzofuro[3,2-c]pyridin-2(1H)-yl]ethyl]-2-methyl-4H-pyrido[1,2-a]pyrimidin-4-one microfine | 16.00 mg |
| Lactose monohydrate DCL11 | 54.20 mg |
| Hydroxypropyl methylcellulose 2208 | 23.40 mg |
| Hydroxypropyl cellulose | 72.00 mg |
| Drum dried waxy maize starch | 9.00 mg |
| Magnesium stearate | 3.6 mg |
| Colloidal anhydrous silica | 1.80 mg |

| Tablet 5 | |
|---|---|
| 3-[2-(3,4-dihydrobenzofuro[3,2-c]pyridin-2(1H)-yl)ethyl]-2-methyl-4H-pyrido[1,2-a]pyrimidin-4-one butanedioate(1:1) | 21.26 mg |
| Lactose monohydrate DCL11 | 103.54 mg |
| Hydroxypropyl methylcellulose 2208 | 41.60 mg |
| Hydroxypropyl cellulose | 128.00 mg |
| Drum dried waxy maize starch | 16.00 mg |
| Magnesium stearate | 6.4 mg |
| Colloidal anhydrous silica | 3.20 mg |

| Tablet 6 | |
|---|---|
| 3-[2-[3,4-dihydrobenzofuro[3,2-c]pyridin-2(1H)-yl]ethyl]-2-methyl-4H-pyrido[1,2-a]pyrimidin-4-one microfine | 16 mg |
| Hydroxypropyl β-cyclodextrin | 200 mg |
| Lactose monohydrate DCL11 | 6.3 mg |
| Hydroxypropyl methylcellulose 2208 | 74.1 mg |
| Hydroxypropyl cellulose | 228 mg |
| Drum dried waxy maize starch | 28.5 mg |
| Magnesium stearate | 11.4 mg |
| Colloidal anhydrous silica | 5.7 mg |
| Ethanol 96% (v/v)** | 363 mg |

*During upscaling of the production process, talc may be replaced by magnesium stearate and lactose monohydrate DCL 11 because of technological reasons.
**does not appear in the final product.

Preparation of Tablet 1 to 5

The active ingredient, hydroxypropyl methylcellulose, hydroxypropyl cellulose, drum dried waxy maize starch and, in case lactose monohydrate 200 mesh was used (Tablets 1 and 2), the lactose filler, were mixed in a planetary mixer, and than compacted using a dry compactor. The compact was broken down, sieved and mixed in a planetary mixer with colloidal anhydrous silica and, in case lactose monohydrate DCL 11 was used (Tablets 3, 4 and 5), the lactose filler. Magnesium stearate was added and mixed. The resulting blend was tabletted using an eccentric press. From the above described tablet preparation procedure, it can be concluded that the lactose filler may be added before or after dry compaction of the polymer blend. This depends on the kind of lactose used, more in particular on the particle size of the lactose.

Preparation of Tablet 6

The active ingredient and hydroxypropyl β-cyclodextrin were dissolved in ethanol 96% (v/v) at 75° C. The resulting solution was evaporated till dry under vacuum. The resulting precipitate was milled and sieved and subsequently mixed with hydroxypropyl methylcellulose, hydroxypropyl cellulose and drum dried waxy maize starch in a planetary mixer, and than compacted using a dry compactor. The compact was broken down, sieved and mixed with colloidal anhydrous silica and lactose in a planetary mixer. Magnesium stearate was added and mixed. The resulting blend was tabletted using an eccentric press.

Coating Preparation

A coating solution was prepared by mixing 69.0% w/w of methylene chloride with 17.30% w/w of ethanol 96% v/v and suspending therein 6.0% w/w of hydroxypropyl methylcellulose 2910 5 mPa·s, 1.5% w/w of polyethylene glycol 400, 4.0% w/w of talc, 1.5% w/w of titanium dioxide and 0.60% w/w of polyethylene glycol 6000. This coating suspension was applied to tablets 3 and 4 in a coating pan, resulting in a coating thickness of 42.8 mg/tablet 3 and 28.4 mg/tablet 4. Optionally, one or more active ingredients can be incorporated in said coating suspension.

In vitro Dissolution Assay a) Cisapride-(L)-tartrate release from tablet 1 and tablet 2 was assessed in vitro at 37° C. by placing each tablet in a beaker containing 400 ml of pH 7.2 McIlvaine buffer or Eurand buffer with 1.5% sodium lauryl sulfate. The medium was stirred with a paddle at 150 revolutions per minute. After 2 hours, 600 ml of buffer (McIlvaine or Eurand) was added to the dissolution medium and the stirring rate was reduced to 100 revolutions per minute. At appropriate time intervals, samples were taken from the release medium and analyzed via UV spectrometry.

A McIlvaine buffer solution (100 ml) (J. Biol. Chem. 49, 183 (1921)) of pH 7.2 consists of 13.05 ml of a citric acid solution (0.1 M) and 86.95 ml of a $Na_2HPO_4.2H_2O$ solution (0.2 M). This McIlvaine buffer solution has a higher ionic strength than the Eurand buffer solution in which dissolution tests are normally performed. At pH 7.2 the ionic strength of a McIlvaine buffer is 0.398.

An Eurand buffer solution (100 ml) of pH 7.2 consists of 190 ml of a sodium hydroxide solution (0.2 N) and 0.087 g of $KH_2PO_4$. The pH of the solution is adjusted to 7.2 with hydrochloric acid 1N and diluted to 100 ml with water. The ionic strength of this Eurand buffer pH 7.2 is 0.076.

Table 1 shows the percentage of cisapride-(L)-tartrate released in either McIlvaine or Eurand buffer as a function of time for tablet 1 and tablet 2. The data illustrate that controlled release of the active ingredient from the tablets is not impeded when the ionic strength of the release medium is increased. They also show that by adapting the amount of hydroxypropyl cellulose and hydroxypropyl methylcellulose, the release profile can be tuned.

b) 3-[2-[3,4-dihydrobenzofuro[3,2-c]pyridin-2(1H)-yl]ethyl]-2-methyl-4H-pyrido-[1,2-a]pyrimidin-4-one release from tablet 3 and tablet 4, both tablets coated as described hereinabove under "Coating preparation", was assessed in vitro at 37° C. by placing each tablet in a basket in a beaker containing 900 ml of 0.1 N HCl. The medium was stirred with the basket at 100 revolutions per minute. At appropriate time intervals, samples were taken from the release medium and analyzed via UV spectrometry.

Table 2 shows the percentage of 3-[2-[3,4-dihydrobenzofuro[3,2-c]pyridin-2(1H)-yl]ethyl]-2-methyl-4H-pyrido[1,2-a]pyrimidin-4-one released as a function of time for coated tablet 3 and coated tablet 4. The data illustrate the controlled release of the active ingredient from the tablets and also show that by adapting the nominal weight and thus size of the tablet, the release profile can be tuned.

c) A tablet having the following composition was prepared:

| | |
|---|---|
| Cisapride-(L)-tartrate | 52.92 mg |
| Lactose | 346.08 mg |
| Hydroxypropyl methylcellulose 2208 | 66.00 mg |
| Hydroxypropyl cellulose | 67.95 mg |
| Magnesium stearate | 2.85 mg |
| Colloidal anhydrous silica | 5.70 mg |
| Talc | 28.60 mg |

The release of cisapride-(L)-tartrate was assessed in vitro at 37° C. by placing the tablet in a basket in a beaker containing 400 ml of pH 7.2 McIlvaine buffer with 1.5% sodium lauryl sulfate. The medium was stirred with the basket at 150 revolutions per minute. At appropriate time intervals, samples were taken from the release medium and analyzed via UV spectrometry.

Table 3 shows the percentage of cisapride-(L)-tartrate released as a function of time. The data illustrate that the active ingredient is released very fast. The formulation lacking the pregelatinized starch was not able to provide a controlled release of the active drug substance; the tablet was not able to gel in the dissolution medium and form an integer matrix network. Instead it disintegrated within a time interval of about 10 to 15 min after immersion in the dissolution medium.

d) The dissolution of 3-[2-[3,4-dihydrobenzofuro[3,2-c]pyridin-2(1H)-yl]ethyl]-2-methyl-4H-pyrido[1,2-a]pyrimidin-4-one from the intimate mixture with hydroxypropyl β-cyclodextrin, prepared as described in the Tablet 6 preparation procedure, was assessed in vitro at 37° C. by introducing 216 mg of said intimate mixture in a beaker containing 300 ml of a pH 7.5 USP buffer. The medium was stirred with a paddle at 100 revolutions per minute. At appropriate time intervals, samples were taken from the dissolution medium and analyzed via UV spectrometry.

USP buffer pH 7.5 was prepared by bringing 6.805 g of $KH_2PO_4$, 204.5 ml of a 0.2 N NaOH solution and 700 ml of distilled water in a 1 liter beaker. After complete dissolution while stirring, the resulting mixture is brought to a volume of 1 liter with distilled water in an appropriate recipient.

Table 4 shows the percentage dissolved 3-[2-[3,4-dihydrobenzofuro[3,2-c]pyridin-2(1H)-yl]ethyl]-2-methyl-4H-pyrido[1,2-a]pyrimidin-4-one as a function of time. The data illustrate that the dissolution of the alkaline active ingredient from the intimate mixture with hydroxypropyl β-cyclodextrin is fast in a medium of pH 7.5.

e) 3-[2-[3,4-dihydrobenzofuro[3,2-c]pyridin-2(1H)-yl]ethyl]-2-methyl-4H-pyrido[1,2-a]pyrimidin-4-one release from tablet 6 was assessed in vitro at 37° C. by placing the tablet in a basket in a beaker containing 600 ml of USP buffer pH 7.5. The medium was stirred with the basket at 100 revolutions per minute. At appropriate time intervals, samples were taken from the release medium and analyzed via UV spectrometry.

Table 5 shows the percentage of 3-[2-[3,4-dihydrobenzofuro[3,2-c]pyridin-2(1H)-yl]ethyl]-2-methyl-4H-pyrido[1,2-a]pyrimidin-4-one released in the USP buffer pH 7.5 as a function of time. The release profile is that of a controlled and regular (zero order) release.

Clinical Trials

Clinical Trial 1

The study described in this example aimed at evaluating and comparing the bioavailability and pharmacokinetics of cisapride after the intake of:

a single dose of 40 mg cisapride (administered as cisapride-(L)-tartrate) in a controlled-release formulation described under tablet formulation 2;

a one-day q.i.d. regimen (4 daily intakes) of the regular marketed 10 mg tablet (Prepulsid®), containing cisapride monohydrate as active ingredient.

In addition, the effects of the concommitant intake of a high-fat meal on the pharmacokinetics of the controlled release formulation was studied.

This explorative trial was an open 3-arm trial in 20 healthy volunteers. Male and female healthy volunteers, aged between 18 and 45 years, were included. The three treatment periods were separated by a washout period of at least 4 days.

Each volunteer took, in a randomised cross-over order, tablet 2, both while fasting and directly after a high-fat meal, and a one-day q.i.d. regimen of Prepulsid®. The latter served as the reference treatment and tablets were taken under "market conditions", i.e. 15 minutes before the main meals and at bed time.

The high-caloric, high-fat meal consisted of three slices of wheaten bread, 15 gram of butter, one scrambled egg and 15 gram of bacon fried in 5 gram of butter, 70 gram of cheese, 150 ml of high fat milk and 150 ml of orange juice (approx. 4000 kJ; 70 g of fat; 30 g protein, 40 g carbohydrate, 350 g water). The cisapride controlled-release tablet was taken within 10 minutes after completing the meal.

Blood samples were drawn pre-dose and at regular time intervals until 48 hours post-dosing.

The plasma concentrations of cisapride were determined by a validated HPLC method. The cardiovascular and laboratory safety and the tolerability of the various treatments were evaluated.

The results of the trial demonstrate that all treatments were safe and well-tolerated.

The detailed pharmacokinetic results are presented in Table 6.

The relative bioavailability of cisapride after intake of tablet 2 under fasting conditions is similar to a one-day q.i.d. course of the regular Prepulsid® tablet. When taken with a high-fat meal, the pharmacokinetic performance of tablet 2 was comparable to the intake under fasting conditions.

Clinical Trial 2

A second explorative trial aimed at evaluating the relative steady-state bioavailability of the controlled-release formulation tablet 2 as compared to a standard treatment with Prepulsid®.

In this 2-arm open study, 18 healthy volunteers took, in a randomised cross-over order, a 6-day course of tablet 2 once daily, and the marketed 10 mg Prepulsid® tablet q.i.d.

All tablets were ingested 15 minutes before a meal (or at bedtime for the fourth tablet of the q.i.d. regimen).

Blood samples were drawn on day 6, starting predose and at regular time intervals until 48 h after the morning intake. The plasma concentrations of cisapride were determined by a validated HPLC method. The cardiovascular and laboratory safety and the tolerability of the various treatments were evaluated.

The results of the trial demonstrate that both chronic treatments were well tolerated and safe.

The detailed pharmacokinetic results are presented in Table 6. Steady state was attained for both treatments. The relative steady-state bioavailability of cisapride after once-daily intake of tablet 2 was similar as compared to q.i.d. treatment with the regular Prepulsid® tablet.

TABLE 1

| | % released cisapride-(L)-tartrate | | | |
|---|---|---|---|---|
| | Tablet 1 | | Tablet 2 | |
| Time (min) | Eurand | McIlvaine | Eurand | McIlvaine |
| 0 | 0.00 | 0.00 | 0.00 | 0.00 |
| 30 | 8.74 | 22.46 | 4.89 | 9.09 |
| 60 | 15.40 | 37.75 | 10.69 | 14.26 |
| 90 | 22.40 | 48.11 | 16.27 | 18.52 |
| 120 | 28.44 | 62.62 | 21.74 | 23.19 |
| 150 | 28.15 | 66.34 | 20.87 | 22.33 |
| 180 | 29.60 | 74.10 | 22.60 | 24.15 |
| 210 | 31.43 | 82.83 | 24.24 | 27.12 |
| 240 | 32.89 | 92.23 | 26.16 | 31.05 |
| 270 | 34.63 | 97.28 | 28.18 | 35.94 |
| 300 | 36.46 | 98.15 | 30.20 | 41.21 |
| 330 | 38.40 | 98.35 | 32.41 | 46.29 |
| 360 | 40.33 | 98.35 | 34.62 | 51.85 |

TABLE 1-continued

| | % released cisapride-(L)-tartrate | | | |
|---|---|---|---|---|
| | Tablet 1 | | Tablet 2 | |
| Time (min) | Eurand | McIlvaine | Eurand | McIlvaine |
| 390 | 42.46 | 98.44 | 36.93 | 57.98 |
| 420 | 44.49 | 98.25 | 39.05 | 67.57 |
| 450 | | | 41.16 | 76.00 |
| 480 | | | 43.18 | 83.48 |
| 510 | | | 45.30 | 88.37 |
| 540 | | | 47.32 | 90.95 |
| 570 | | | 49.34 | 92.58 |
| 600 | | | 51.36 | 94.21 |
| 630 | | | 53.38 | 95.46 |
| 660 | | | 55.11 | 96.42 |
| 690 | | | 56.84 | 97.18 |
| 720 | | | 58.57 | 97.66 |
| 750 | | | 60.49 | 98.05 |
| 780 | | | 62.22 | 98.24 |
| 810 | | | 64.05 | 98.33 |
| 840 | | | 65.69 | 98.53 |
| 870 | | | 67.32 | 98.81 |
| 900 | | | 69.15 | 98.91 |

TABLE 2

| | % released 3-[2-[3,4-dihydrobenzofuro[3,2-c]pyridin-2(1H)-yl]ethyl]-2-methyl-4H-pyrido[1,2-a]pyrimidin-4-one | |
|---|---|---|
| Time (min) | Coated Tablet 3 | Coated Tablet 4 |
| 0 | 0.00 | 0.00 |
| 30 | 12.59 | 15.00 |
| 60 | 21.04 | 24.97 |
| 90 | 27.73 | 33.46 |
| 120 | 33.72 | 41.44 |
| 150 | 39.37 | 48.64 |
| 180 | 44.84 | 55.29 |
| 210 | 49.76 | 61.29 |
| 240 | 54.63 | 67.24 |
| 270 | 59.33 | 72.36 |
| 300 | 63.56 | 77.12 |
| 330 | 67.40 | 81.64 |
| 360 | 70.98 | 85.66 |
| 390 | 74.34 | 89.21 |
| 420 | 77.49 | 92.44 |
| 450 | 80.46 | 94.84 |
| 480 | 83.05 | 96.92 |
| 510 | 85.51 | 98.72 |
| 540 | 87.75 | 99.96 |
| 570 | 89.78 | 100.84 |
| 600 | 91.54 | 101.39 |
| 630 | 93.23 | 101.49 |
| 660 | 94.73 | 101.44 |
| 690 | 95.68 | 101.53 |
| 720 | 96.63 | 101.39 |
| 750 | 97.11 | 101.44 |
| 780 | 97.36 | 101.49 |
| 810 | 97.45 | 101.58 |
| 840 | 97.58 | 101.53 |
| 870 | 97.58 | 101.53 |
| 900 | 97.67 | 101.58 |

TABLE 3

| Time (min) | % released active ingredient |
|---|---|
| 0 | 0.00 |
| 30 | 89.31 |
| 60 | 93.44 |
| 90 | 94.19 |
| 120 | 93.81 |

TABLE 4

| Time (min) | % dissolved active ingredient |
|---|---|
| 0 | 0.00 |
| 5 | 100.88 |
| 15 | 101.44 |
| 30 | 101.63 |

TABLE 5

| Time (min) | % released active ingredient |
|---|---|
| 0 | 0.00 |
| 30 | 7.98 |
| 60 | 11.99 |
| 90 | 15.30 |
| 120 | 17.74 |
| 150 | 20.03 |
| 180 | 21.94 |
| 240 | 25.80 |
| 270 | 27.53 |
| 300 | 29.63 |
| 330 | 31.20 |
| 360 | 33.26 |
| 390 | 34.13 |
| 420 | 35.96 |

TABLE 6

Pharmacokinetic data for tablet 2

| | Fasting | Fed | Steady state |
|---|---|---|---|
| $t_{max}$, h | 9.6 ± 4.5 | 6.4 ± 3.2 | 4.2 ± 3.2 |
| $C_{max}$, ng/ml | 59.3 ± 18.9 | 74.9 ± 17.5 | 85.9 ± 32.9 |
| $AUC_{24\,h}$, ng·h/ml | 968 ± 293 | 1012 ± 242 | 1305 ± 541 |
| $AUC_{48\,h}$, ng·h/ml | 1286 ± 383 | 1288 ± 346 | 1798 ± 783 |
| $AUC_\infty$, ng·h/ml | 1373 ± 401 | 1349 ± 363 | 1982 (simulated) |

Bioequivalence Fed versus Fasting

| | |
|---|---|
| $F_{rel}$ Cmax | 1.26 |
| $F_{rel}$ AUC24 h | 1.05 |
| $F_{rel}$ AUC48 h | 1.00 |
| $F_{rel}$ AUC$_\infty$ | 0.98 |

Bioequivalence versus Reference (Prepulsid ® q.i.d.)

| | | | |
|---|---|---|---|
| $F_{rel} C_{max}$ | 0.84 | 1.05 | 0.99 |
| $F_{rel} AUC_{24\,h}$ | 0.89 | 0.93 | 0.97 |
| $F_{rel} AUC_{48\,h}$ | 0.93 | 0.93 | 1.03 |
| $F_{rel} AUC_\infty$ | 0.96 | 0.94 | 1.10 |

The invention claimed is:

1. A hydrophilic controlled release solid tablet formulation comprising a matrix comprising, as a substantially homogeneous admixture:
   about 5% to less than 80%, by weight of the tablet, of pregelatinized starch
   an active ingredient that is 9-hydroxyrisperidone, a pharmaceutically acceptable acid addition salt thereof, an N-oxide form thereof, or a stereochemically isomeric form thereof, and
   one or more viscous hydrophilic polymers,
   wherein said controlled release solid tablet formulation allows at least a two-fold reduction in dosing frequency, an increase in patient compliance, or an increase in therapeutic performance, as compared to a conventional 9-hydroxyrisperidone dosage form.

2. The controlled release solid tablet formulation of claim 1, wherein said one or more hydrophilic polymers are selected from the group consisting of alkylcellulose, hydroxyalkylcellulose, hydroxyalkylalkylcellulose, carboxyalkylcellulose, alkali metal salts of carboxyalkylcellulose, natural, semi synthetic or synthetic polysaccharide, polyacrylic acid and salts thereof, polymethacrylic acid and the salts thereof, polyvinyl alcohol, polyvinylpyrrolidone, and polyalkylene oxides.

3. The controlled release solid tablet formulation of claim 1, wherein said one or more hydrophilic polymers are selected from the group consisting of hydroxypropyl cellulose and hydroxypropylmethylcellulose.

4. The controlled release solid tablet formulation of claim 3, wherein said hydroxypropylmethylcellulose has a viscosity in a range from about 3,500 mPa·s to about 100,000 mPa·s.

5. The controlled release solid tablet formulation of claim 3, wherein said hydroxypropylcellulose has a viscosity of less than about 1,500 mPa·s.

6. The controlled release solid tablet formulation of claim 1, wherein said one or more hydrophilic polymers are present in an amount from about 0.01 to about 80% by weight of the tablet.

7. The controlled release solid tablet formulation of claim 1, wherein at least two hydrophilic polymers are present in said formulation.

8. The controlled release solid tablet formulation of claim 7, wherein said at least two hydrophilic polymers are hydroxypropylcellulose and hydroxypropylmethylcellulose.

9. The controlled release solid tablet formulation of claim 8, wherein a ratio of said hydroxypropylcellulose to said hydroxypropylmethylcellulose ranges from 1:5 to 5:1.

10. The controlled release solid tablet formulation of claim 1, wherein said pregelatinized starch is present at about 5% (w/w), by weight of the tablet.

11. The controlled release solid tablet formulation of claim 1, wherein said pregelatinized starch is present at about 5% to about 15%, by weight of the tablet.

12. A method of providing controlled release of 9-hydroxyrisperidone, a pharmaceutically acceptable acid addition salt thereof, an N-oxide form thereof, or a stereochemically isomeric form thereof, in a subject, comprising administering the controlled release solid tablet formulation of claim 1 to said subject.

13. A method of preparing a controlled release solid tablet formulation comprising mixing 9-hydroxyrisperidone, a pharmaceutically acceptable acid addition salt thereof, an N-oxide form thereof, or a stereochemically isomeric form thereof with about 5% to less than 80%, by weight of the tablet, of pregelatinized starch and one or more hydrophilic polymers, to provide a substantially homogeneous admixture thereof, such that said controlled release solid tablet formulation allows at least a two-fold reduction in dosing frequency, an increase in patient compliance, or an increase in therapeutic performance, as compared to a conventional 9-hydroxyrisperidone dosage form.

14. The controlled release solid tablet formulation according to claim 1 wherein the tablet consists essentially of an optional coating and a controlled release matrix comprising a substantially homogeneous admixture comprising said active ingredient, said one or more viscous hydrophilic polymers, and said pregelatinized starch.

* * * * *

UNITED STATES PATENT AND TRADEMARK OFFICE
CERTIFICATE OF CORRECTION

| | | |
|---|---|---|
| PATENT NO. | : 8,591,945 B2 | Page 1 of 1 |
| APPLICATION NO. | : 12/416219 | |
| DATED | : November 26, 2013 | |
| INVENTOR(S) | : Vandercruys et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 871 days.

Signed and Sealed this
Fourteenth Day of April, 2015

Michelle K. Lee
*Director of the United States Patent and Trademark Office*